United States Patent
Guillet et al.

(10) Patent No.: US 8,932,599 B2
(45) Date of Patent: Jan. 13, 2015

(54) SYNTHETIC GENE CONSTRUCT CODING FOR AN HIV1 GAG AND USE THEREOF FOR OBTAINING ANTI-HIV-1 VACCINES

(75) Inventors: Jean-Gérard Guillet, Paris (FR); Caterina Riconda Guillet, legal representative, Paris (FR); Yves Levy, Creteil (FR); Jean-Marc Balloul, Illkirch Graffenstaden Cedex (FR); Doris Schmitt, Illkirch Graffenstaden Cedex (FR)

(73) Assignees: Institut National de la Sante et de la Recherche Medicale, Paris (FR); Centre National de la Recherche Scientifique, Paris (FR); Universite Paris Est Creteil Val de Marne, Creteil (FR)

( * ) Notice: Subject to any disclaimer, the term of this patent is extended or adjusted under 35 U.S.C. 154(b) by 591 days.

(21) Appl. No.: 13/063,277

(22) PCT Filed: Sep. 10, 2009

(86) PCT No.: PCT/FR2009/051704
§ 371 (c)(1),
(2), (4) Date: Mar. 10, 2011

(87) PCT Pub. No.: WO2010/029260
PCT Pub. Date: Mar. 18, 2010

(65) Prior Publication Data
US 2011/0171250 A1 Jul. 14, 2011

(51) Int. Cl.
*A61K 39/21* (2006.01)
*C07H 21/04* (2006.01)
*C07K 14/005* (2006.01)
*C12N 15/86* (2006.01)
*A61K 39/00* (2006.01)

(52) U.S. Cl.
CPC .............. *C07K 14/005* (2013.01); *C12N 15/86* (2013.01); *A61K 2039/5256* (2013.01); *C07K 2319/00* (2013.01); *C12N 2710/24143* (2013.01); *C12N 2740/16122* (2013.01)
USPC .................. 424/188.1; 424/208.1; 536/23.72

(58) Field of Classification Search
None
See application file for complete search history.

(56) References Cited

U.S. PATENT DOCUMENTS

2008/0274992 A1* 11/2008 Excler et al. .................... 514/44
2011/0104199 A1* 5/2011 Moss et al. ................. 424/199.1

FOREIGN PATENT DOCUMENTS

EP       1 921 146       5/2008
WO    WO-2005/030964    4/2005

OTHER PUBLICATIONS

Gallo, R. C., Dec. 2005, The end or the beginning of the drive to an HIV-preventive vaccine: a view from over 20 years, The Lancet, 366:1894-1898.*
Barouch, D. H., Oct. 2008, Challenges in the development of an HIV-1 vaccine, Nature 455:613-618.*
Walker, B. D., and D. R. Burton, May 2008, Toward an AIDS vaccine, Science 320:760-764.*
International Search Report for PCT/FR2009/051704.
Pr. Yves Levy & Anne de Sauniere, "La recherche vaccinale de l'ANRS—Prospective 2007-2010" [Online] Feb. 9, 2007, XP002511934, Retrieved from the Internet: URL: http://www.anrs.fr/index.php/anrs/content/download/1685/10599/file/6-La%20recherche%20vaccinale%20de%201'ANRS.pps>[retrieved on Jan. 23, 2009] p. 27-p. 28.
Smith et al, "DNA/MVA vaccine for HIV type 1: Effects of codon-optimization and the expression of aggregates or virus-like particles on the immunogenicity of the DNA prime", Dec. 2004, pp. 1335-1347, vol. 20, No. 12, Aids Research and Human Retroviruses.

* cited by examiner

*Primary Examiner* — Jeffrey Parkin
(74) *Attorney, Agent, or Firm* — B. Aaron Schulman, Esq.; Stites & Harbison, PLLC.

(57) ABSTRACT

The invention relates to a synthetic gene coding for the Gag protein of the human immunodeficiency virus HIV-1. Said gene may optionally be fused with one or more other HIV sequences. The invention may notably be used within the scope of obtaining anti-HIV vaccines.

11 Claims, 11 Drawing Sheets

Figure 1:
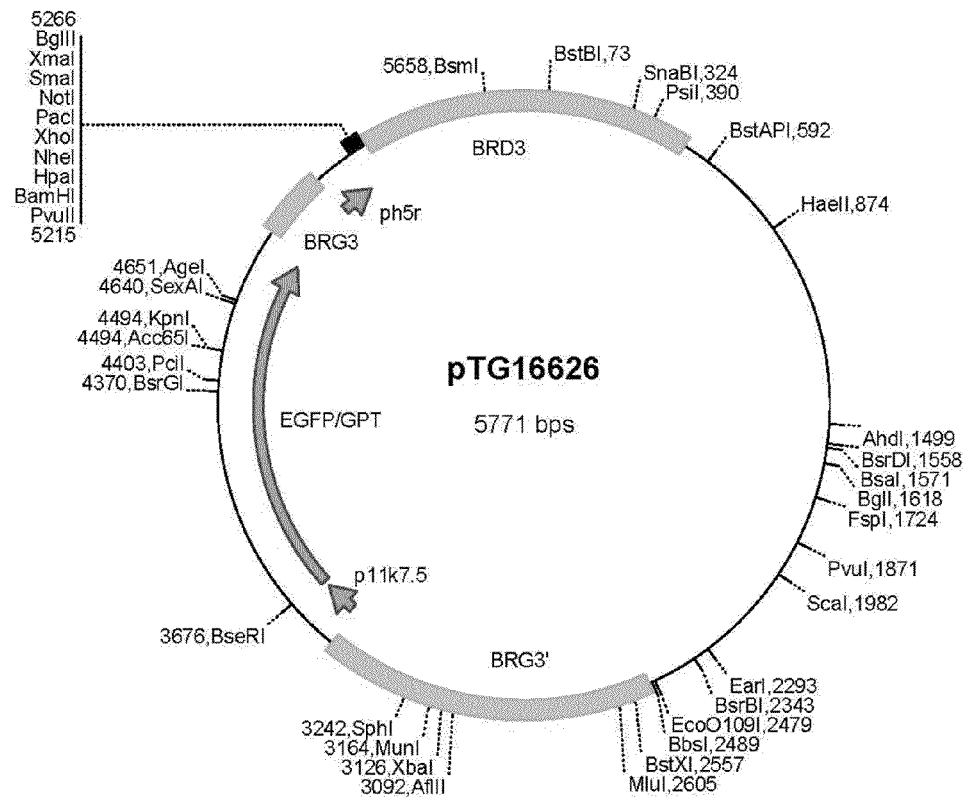

```
              1                                                  50
F-PTG17401    AAATAAATCA TATAAAAAAT GATTTCATGA TTAAACCATG TTGTGAAAAA 51                                                100
F-PTG17401    GTCAAGAACG TTCACATTGG CGGACAATCT AAAAACAATA CAGTGATTGC 101                                               150
F-PTG17401    AGATTTGCCA TATATGGATA ATGCGGTATC CGATGTATGC AATTCACTGT 151                                               200
F-PTG17401    ATAAAAAGAA TGTATCAAGA ATATCCAGAT TTGCTAATTT GATAAAGATA 201                                               250
F-PTG17401    GATGACGATG ACAAGACTCC TACTGGTGTA TATAATTATT TTAAACCTAA 251                                               300
F-PTG17401    AGATGCCATT CCTGTTATTA TATCCATAGG AAAGGATAGA GATGTTTGTG 301                                               350
F-PTG17401    AACTATTAAT CTCATCTGAT AAAGCGTGTG CGTGTATAGA GTTAAATTCA 351                                               400
F-PTG17401    TATAAAGTAG CCATTCTTCC CATGGATGTT TCCTTTTTTA CCAAAGGAAA 401                                               450
F-PTG17401    TGCATCATTG ATTATTCTCC TGTTTGATTT CTCTATCGAT GCGGCACCTC 451                                               500
F-PTG17401    TCTTAAGAAG TGTAACCGAT AATAATGTTA TTATATCTAG ACACCAGCGT 501                                               550
F-PTG17401    CTACATGACG AGCTTCCGAG TTCCAATTGG TTCAAGTTTT ACATAAGTAT 551                                               600
F-PTG17401    AAAGTCCGAC TATTGTTCTA TATTATATAT GGTTGTTGAT GGATCTGTGA 601                                               650
F-PTG17401    TGCATGCAAT AGCTGATAAT AGAACTTACG CAAATATTAG CAAAAATATA 651                                               700
F-PTG17401    TTAGACAATA CTACAATTAA CGATGAGTGT AGATGCTGTT ATTTTGAACC 701                                               750
F-PTG17401    ACAGATTAGG ATTCTTGATA GAGATGAGAT GCTCAATGGA TCATCGTGTG 751                                               800
F-PTG17401    ATATGAACAG ACATTGTATT ATGATGAATT TACCTGATGT AGGCGAATTT 801                                               850
F-PTG17401    GGATCTAGTA TGTTGGGGAA ATATGAACCT GACATGATTA AGATTGCTCT 851                                               900
F-PTG17401    TTCGGTGGCT GGTGAGCTCG GATCTAAGCT TGTCGACATA AAAATATAGT
```

FIG.3 (Beginning)

| | 901 | | | | 950 |
|---|---|---|---|---|---|
| F-PTG17401 | AGAATTTCAT | TTGTTTTTTT | CTATGCTATA | AATAGGATCG | ATCCGATAAA |
| | 951 | | | | 1000 |
| F-PTG17401 | GTGAAAAATA | ATTCTAATTT | ATTGCACGGT | AAGGAAGTAG | AATCATAAAG |
| | 1001 | | | | 1050 |
| F-PTG17401 | AAAAGCTTCT | GCAGGTCGAC | ATGGTGAGCA | AGGGCGAGGA | GCTGTTCACC |
| | 1051 | | | | 1100 |
| F-PTG17401 | GGGGTGGTGC | CCATCCTGGT | CGAGCTGGAC | GGCGACGTAA | ACGGCCACAA |
| | 1101 | | | | 1150 |
| F-PTG17401 | GTTCAGCGTG | TCCGGCGAGG | GCGAGGGCGA | TGCCACCTAC | GGCAAGCTGA |
| | 1151 | | | | 1200 |
| F-PTG17401 | CCCTGAAGTT | CATCTGCACC | ACCGGCAAGC | TGCCCGTGCC | CTGGCCCACC |
| | 1201 | | | | 1250 |
| F-PTG17401 | CTCGTGACCA | CCCTGACCTA | CGGCGTGCAG | TGCTTCAGCC | GCTACCCCGA |
| | 1251 | | | | 1300 |
| F-PTG17401 | CCACATGAAG | CAGCACGACT | TCTTCAAGTC | CGCCATGCCC | GAAGGCTACG |
| | 1301 | | | | 1350 |
| F-PTG17401 | TCCAGGAGCG | CACCATCTTC | TTCAAGGACG | ACGGCAACTA | CAAGACCCGC |
| | 1351 | | | | 1400 |
| F-PTG17401 | GCCGAGGTGA | AGTTCGAGGG | CGACACCCTG | GTGAACCGCA | TCGAGCTGAA |
| | 1401 | | | | 1450 |
| F-PTG17401 | GGGCATCGAC | TTCAAGGAGG | ACGGCAACAT | CCTGGGGCAC | AAGCTGGAGT |
| | 1451 | | | | 1500 |
| F-PTG17401 | ACAACTACAA | CAGCCACAAC | GTCTATATCA | TGGCCGACAA | GCAGAAGAAC |
| | 1501 | | | | 1550 |
| F-PTG17401 | GGCATCAAGG | TGAACTTCAA | GATCCGCCAC | AACATCGAGG | ACGGCAGCGT |
| | 1551 | | | | 1600 |
| F-PTG17401 | GCAGCTCGCC | GACCACTACC | AGCAGAACAC | CCCCATCGGC | GACGGCCCCG |
| | 1601 | | | | 1650 |
| F-PTG17401 | TGCTGCTGCC | CGACAACCAC | TACCTGAGCA | CCCAGTCCGC | CCTGAGCAAA |
| | 1651 | | | | 1700 |
| F-PTG17401 | GACCCCAACG | AGAAGCGCGA | TCACATGGTC | CTGCTGGAGT | TCGTGACCGC |
| | 1701 | | | | 1750 |
| F-PTG17401 | CGCCGGGATC | ACTCTCGGCA | TGGACGAGCT | GTACAAGAGC | GAAAAATACA |
| | 1751 | | | | 1800 |
| F-PTG17401 | TCGTCACCTG | GGACATGTTG | CAGATCCATG | CACGTAAACT | CGCAAGCCGA |

FIG.3 (Continuation)

```
              1801                                          1850
F-PTG17401    CTGATGCCTT CTGAACAATG GAAAGGCATT ATTGCCGTAA GCCGTGGCGG 1851                                          1900
F-PTG17401    TCTGGTACCG GGTGCGTTAC TGGCGCGTGA ACTGGGTATT CGTCATGTCG 1901                                          1950
F-PTG17401    ATACCGTTTG TATTTCCAGC TACGATCACG ACAACCAGCG CGAGCTTAAA 1951                                          2000
F-PTG17401    GTGCTGAAAC GCGCAGAAGG CGATGGCGAA GGCTTCATCG TTATTGATGA 2001                                          2050
F-PTG17401    CCTGGTGGAT ACCGGTGGTA CTGCGGTTGC GATTCGTGAA ATGTATCCAA 2051                                          2100
F-PTG17401    AAGCGCACTT TGTCACCATC TTCGCAAAAC CGGCTGGTCG TCCGCTGGTT 2101                                          2150
F-PTG17401    GATGACTATG TTGTTGATAT CCCGCAAGAT ACCTGGATTG AACAGCCGTG 2151                                          2200
F-PTG17401    GGATATGGGC GTCGTATTCG TCCCGCCAAT CTCCGGTCGC TAATCTTTTC 2201                                          2250
F-PTG17401    AACGCCTGGC ACTGCCGGGC GTTGTTCTTT TTAACTTCCC TGCATAATTA 2251                                          2300
F-PTG17401    ACGATGAGTG TAGATGCTGT TATTTTGAAC CACAGATTAG GATTCTTGAT 2301                                          2350
F-PTG17401    AGAGATGAGA TGCTCAATGG ATCATCGTGT GATATGAACA GACATTGTAT 2351                                          2400
F-PTG17401    TATGATGAAT TTACCTGATG TAGGCGAATT TGGATCTAGT ATGTTGGGGA 2401                                          2450
F-PTG17401    AATATGAACC TGACATGATT AAGATTGCTC TTTCGGTGGC TGGTGAGCTC 2451                                          2500
F-PTG17401    GGATCTTTTA TTCTATACTT AAAAAATGAA AATAAATACA AAGGTTCTTG 2501                                          2550
F-PTG17401    AGGGTTGTGT TAAATTGAAA GCGAGAAATA ATCATAAATT ATTTCATTAT 2551                                          2600
F-PTG17401    CGCGATATCC GTTAAGTTTG CTGCAGCTGG ATCCATGGGC GCCAGGGCCA 2601                                          2650
F-PTG17401    GCGTGCTGAG CGGAGGCGAG CTGGACAGGT GGGAGAAGAT CAGGCTGAGG 2651                                          2700
F-PTG17401    CCTGGAGGCA AGAAGAAGTA TAAGCTGAAG CACATCGTGT GGGCCAGCAG
```

FIG.3 (Continuation)

```
F-PTG17401      2701                                                    2750
                GGAGCTGGAG AGGTTCGCCG TGAACCCTGG CCTGCTGGAG ACCAGCGAGG

F-PTG17401      2751                                                    2800
                GCTGCAGGCA GATCCTGGGC CAGCTGCAGC CCAGCCTGCA GACCGGCAGC

F-PTG17401      2801                                                    2850
                GAGGAGCTGA GGAGCCTGTA CAACACCGTG GCCACCCTGT ACTGCGTGCA

F-PTG17401      2851                                                    2900
                CCAGAGGATC GAGATCAAGG ACACCAAGGA GGCCCTGGAC AAGATCGAGG

F-PTG17401      2901                                                    2950
                AGGAGCAGAA CAAGTCCAAG AAGAAGGCCC AGCAGGCTGC TGCCGACACC

F-PTG17401      2951                                                    3000
                GGCCACAGCA GCCAGGTGAG CCAGAACTAC CCTATCGTGC AGAACATCCA

F-PTG17401      3001                                                    3050
                GGGCCAGATG GTGCACCAGG CCATCAGCCC TAGGACCCTG AACGCCTGGG

F-PTG17401      3051                                                    3100
                TGAAGGTGGT GGAGGAGAAG GCCTTCAGCC CTGAGGTGAT CCCTATGTTC

F-PTG17401      3101                                                    3150
                AGCGCCCTGA GCGAGGGAGC CACACCTCAG GACCTGAACA CCATGCTGAA

F-PTG17401      3151                                                    3200
                CACCGTGGGA GGCCACCAGG CCGCCATGCA GATGCTGAAG GAGACCATCA

F-PTG17401      3201                                                    3250
                ACGAGGAGGC TGCCGAGTGG GACAGGGTGC ACCCTGTGCA CGCTGGACCC

F-PTG17401      3251                                                    3300
                ATCGCTCCAG GCCAGATGAG GGAGCCCAGA GGCAGCGACA TCGCCGGCAC

F-PTG17401      3301                                                    3350
                CACCAGCACC CTGCAGGAGC AGATCGGCTG GATGACCAAC AACCCTCCCA

F-PTG17401      3351                                                    3400
                TCCCTGTGGG CGAAATCTAC AAGAGGTGGA TCATCCTGGG CCTGAACAAG

F-PTG17401      3401                                                    3450
                ATCGTGAGGA TGTACAGCCC TACCAGCATC CTGGATATCA GGCAGGGCCC

F-PTG17401      3451                                                    3500
                TAAAGAGCCC TTCAGGGACT ACGTGGACAG GTTCTACAAG ACCCTGAGAG

F-PTG17401      3501                                                    3550
                CCGAGCAGGC CAGCCAGGAG GTGAAGAACT GGATGACCGA GACCCTGCTG

F-PTG17401      3551                                                    3600
                GTGCAGAACG CCAACCCTGA CTGCAAGACC ATCCTGAAGG CCCTGGGACC
```

FIG.3 (Continuation)

```
F-PTG17401    3601                                                        3650
              TGCTGCCACC CTGGAGGAGA TGATGACCGC CTGCCAGGGC GTGGGAGGCC

F-PTG17401    3651                                                        3700
              CAGGCCACAA GGCCAGGGTG CTGGCCGAGG CCATGAGCCA GGTGACCAAC

F-PTG17401    3701                                                        3750
              ACCGCCACCA TCATGATGCA GAGAGGCAAC TTCAGGAACC AGAGGAAGAT

F-PTG17401    3751                                                        3800
              GGTGAAGTGC TTCAACTGCG GCAAGGAGGG CCACACCGCC AGGAACTGCA

F-PTG17401    3801                                                        3850
              GGGCTCCCAG GAAGAAGGGC TGCTGGAAGT GCGGCAAGGA GGGCCACCAG

F-PTG17401    3851                                                        3900
              ATGAAGGACT GCACCGAGAG GCAGGCCAAC TTCCTGGGCA AGATCTGGCC

F-PTG17401    3901                                                        3950
              CAGCTACAAG GGCAGGCCAG GCAACTTCCT GCAGAGCAGG CCCGAGCCCA

F-PTG17401    3951                                                        4000
              CCGCTCCACC TTTCCTGCAG AGCAGGCCCG AGCCCACCGC TCCTCCTGAG

F-PTG17401    4001                                                        4050
              GAGAGCTTCA GGAGCGGCGT GGAGACAACC ACCCCTCCTC AGAAGCAGGA

F-PTG17401    4051                                                        4100
              GCCCATCGAC AAGGAGCTGT ACCCTCTGAC CAGCCTGAGG AGCCTGTTCG

F-PTG17401    4101                                                        4150
              GCAACGACCC TAGCAGCCAG GAGTCGACCG GGCCACTAAC AGAAGAAGCA

F-PTG17401    4151                                                        4200
              GAGCTAGAAC TGGCAGAAAA CAGAGAGATT CTAAAAGAAC CAGTACATGG

F-PTG17401    4201                                                        4250
              AGTGTATTAT GACCCATCAA AAGACTTAAT AGCAGAAATA CAGAAGCAGG

F-PTG17401    4251                                                        4300
              GGCAAGGCCA ATGGACATAT CAAATTTATC AAGAGCCATT TAAAAATCTG

F-PTG17401    4301                                                        4350
              AAAACAGGAA TGGAGTGGAG ATTTGATTCT AGATTAGCAT TCATCACGT

F-PTG17401    4351                                                        4400
              AGCTAGAGAA TTACATCCTG AATATTTTAA AAATTGTAAG CTTATGGCAA

F-PTG17401    4401                                                        4450
              TATTCCAAAG TAGCATGACA AAAATCTTAG AGCCTTTTAG AAAACAAAAT

F-PTG17401    4451                                                        4500
              CCAGACATAG TTATCTATCA ATACATGGAT GATTTGTATG TAGGATCTGA
```

FIG.3 (Continuation)

```
           4501                                                    4550
F-PTG17401 CTTAGAAATA GGGCAGCATA GAACAAAAAT AGAGGAGCTG AGACAACATC 4551                                                    4600
F-PTG17401 TGTTGAGGTG GGGACTTACA ACCATGGTAG GTTTTCCAGT AACACCTCAA 4601                                                    4650
F-PTG17401 GTACCTTTAA GACCAATGAC TTACAAAGCA GCTGTAGATC TTTCTCACTT 4651                                                    4700
F-PTG17401 TTTAAAAGAA AAAGGAGGTT TAGAAGGGCT AATTCATTCT CAACGAAGAC 4701                                                    4750
F-PTG17401 AAGATATTCT TGATTTGTGG ATTTATCATA CACAAGGATA TTTTCCTGAT 4751                                                    4800
F-PTG17401 TGGCAGAATT ACACACCAGG ACCAGGAGTC AGATACCCAT TAACCTTTGG 4801                                                    4850
F-PTG17401 TTGGTGCTAC AAGCTAGTAC CAATGATTGA GACTGTACCA GTAAAATTAA 4851                                                    4900
F-PTG17401 AGCCAGGAAT GGATGGCCCA AAAGTTAAAC AATGGCCATT GACAGAAGAA 4901                                                    4950
F-PTG17401 AAAATAAAAG CATTAGTAGA AATTTGTACA GAGATGGAAA AGGAAGGGAA 4951                                                    5000
F-PTG17401 AATTTCAAAA ATTGGGCCTT AAGCGGCCGC CCGGGAGAT CTCGATCCGG 5001                                                    5050
F-PTG17401 AAAGTTTTAT AGGTAGTTGA TAGAACAAAA TACATAATTT TGTAAAAATA 5051                                                    5100
F-PTG17401 AATCACTTTT TATACTAATA TGACACGATT ACCAATACTT TTGTTACTAA 5101                                                    5150
F-PTG17401 TATCATTAGT ATACGCTACA CCTTTTCCTC AGACATCTAA AAAAATAGGT 5151                                                    5200
F-PTG17401 GATGATGCAA CTTATCATG TAATCGAAAT AATACAAATG ACTACGTTGT 5201                                                    5250
F-PTG17401 TATGAGTGCT TGGTATAAGG AGCCCAATTC CATTATTCTT TTAGCTGCTA 5251                                                    5300
F-PTG17401 AAAGCGACGT CTTGTATTTT GATAATTATA CCAAGGATAA AATATCTTAC 5301                                                    5350
F-PTG17401 GACTCTCCAT ACGATGATCT AGTTACAACT ATCACAATTA AATCATTGAC 5351                                                    5400
F-PTG17401 TGCTAGAGAT GCCGGTACTT ATGTATGTGC ATTCTTTATG ACATCGCCTA
```

FIG.3 (Continuation)

```
              5401                                                 5450
F-PTG17401    CAAATGACAC TGATAAAGTA GATTATGAAG AATACTCCAC AGAGTTGATT 5451                                                 5500
F-PTG17401    GTAAATACAG ATAGTGAATC GACTATAGAC ATAATACTAT CTGGATCTAC 5501                                                 5550
F-PTG17401    ACATTCACCG GAAACTAGTT CTGAGAAACC TGATTATATA GATAATTCTA 5551                                                 5600
F-PTG17401    ATTGCTCGTC GGTATTCGAA ATCGCGACTC CGGAACCAAT TACTGATAAT 5601                                                 5650
F-PTG17401    GTAGAAGATC ATACAGACAC CGTCACATAC ACTAGTGATA GCATTAATAC 5651                                                 5700
F-PTG17401    AGTAAGTGCA TCATCTGGAG AATCCACAAC AGACGAGACT CCGGAACCAA 5701                                                 5750
F-PTG17401    TTACTGATAA AGAAGAAGAT CATACAGTTA CAGACACTGT CTCATACACT 5751                                                 5800
F-PTG17401    ACAGTAAGTA CATCATCTGG AATTGTCACT ACTAAATCAA CCACCGATGA 5801                                                 5850
F-PTG17401    TGCGGATCTT TATGATACGT ACAATGATAA TGATACAGTA CCATCAACTA 5851                                                 5900
F-PTG17401    CTGTAGGCGG TAGTACAACC TCTATTAGCA ATTATAAAAC CAAGGACTTT 5901                                                 5950
F-PTG17401    GTAGAAATAT TTGGTATTAC CGCATTAATT ATATTGTCGG CCGTGGCAAT 5951                                                 6000
F-PTG17401    ATTCTGTATT ACATATTATA TATATAATAA ACGTTCACGT AAATACAAAG
```

FIG.3 (End)

SYNTHETIC GENE CONSTRUCT CODING FOR AN HIV1 GAG AND USE THEREOF FOR OBTAINING ANTI-HIV-1 VACCINES

The present invention relates to a synthetic gene coding for the Gag (p55) protein of HIV-1 (human immunodeficiency virus), and to its use for obtaining anti-HIV vaccines.

The anti-HIV vaccines presently being developed are based on different approaches (for a review cf. for example NABEL, Nature, 410, 1002-7, 2001) among which mention will be made of the use of expression vectors, notably recombinant viral vectors, into which are inserted portions of the HIV genome coding for polypeptides bearing epitopes recognized by antibodies, or by anti-HIV cytotoxic T lymphocytes (CTLs), and therefore potentially mediators of an anti-HIV humoral and/or cellular immune response.

Among the regions of the HIV genome, the most used within this scope, appear those derived from the gag gene. The Gag protein notably forms an immunogen particularly interesting for inducing, not only antibody response but also a CTL response.

Generally, in order to induce the widest possible immune response, different portions of the HIV genome, the expression of which from this vector is carried in the form of a fusion protein form, are associated in a same vector. Mention will be made as examples of fusion proteins associating the Gag protein with regions of the Pol protein, of the Nef protein, and/or of the Env protein.

A problem encountered during the use of these expression vectors lies in the low level of expression of the HIV genes which are inserted therein, and in the lack of stability of this expression.

An approach presently used for increasing the level of expression of the HIV genes consists of optimizing their coding sequence, in order to suppress inhibiting nucleotide sequences (INS) rich in AT, notably present in the gag, pol and env genes and for modifying the use of the codons, by replacing certain of the initial HIV codons with synonym codons preferentially used in human cells (QIU et al., J Virol, 73, 9145-52, 1999; Zur Megede et al., J. Virol. 74, 2628-35, 2000; Kotsopoulou et al., J Virol, 74, 4839-52, 2000).

With this approach it is possible to increase the expression level, but the stability of this expression still remains a problem, notably in the case of the gag gene.

The inventors have issued the assumption that the presence of many poly C, poly G or poly GC patterns in the sequences used for expressing the gag protein played a role in this lack of stability, and have proceeded with additional optimization in order to suppress the poly C or poly G patterns with a size of more than 3 nucleotides and the poly GC patterns with a size of more than 8 nucleotides.

Accordingly the object of the present invention is a polynucleotide coding for the HIV-1 Gag (p55) protein, characterized in that it is defined by the sequence SEQ ID NO: 1.

The object of the present invention is also a recombinant polynucleotide, comprising the sequence SEQ ID NO:1. Advantageously, said recombinant polynucleotide codes for a fusion protein comprising the Gag (p55) protein of HIV-1, fused with one or more other HIV polypeptides.

Preferably, said other HIV polypeptide(s) is(are) selected from the Pol protein, the Nef protein, the Env protein, or any fragment of said proteins bearing at least one epitope recognized by anti-HIV antibodies, or by anti-HIV cytotoxic T lymphocytes (CTLs). As non-limiting examples of such fragments, mention will be made of the fragments of the Pol protein homologous to the fragments 172-219, 325-383, and 461-519 of the Pol protein of the Bru/LAI HIV-1 isolate, and of the fragments of the Nef protein homologous to fragments 66-147 and 182-206 of the Nef protein of the Bru/LAI HIV-1 isolate. The Bru/LAI HIV-1 isolate is listed in the catalog of Los Alamos under the accession number K02013. Unless specified otherwise, the numbering of the amino acids of the sequences of the proteins of this isolate is used here as a reference, when peptide fragments are defined by their localization with respect to the sequence of a HIV protein.

According to a preferred embodiment of the present invention, said recombinant polynucleotide is defined by the sequence SEQ ID NO: 2.

It codes for the fusion protein gag-nef-pol, defined by the sequence SEQ ID NO: 3.

This fusion protein, which is also part of the object of the present invention, comprises, in addition to the totality of the Gag (p55) protein (amino acids 1-512 of the sequence SEQ ID NO: 3), fragments corresponding to the fragments 461-519, 325-383, and 172-219 of the Pol protein of the Bru/LAI HIV-1 isolate (these fragments are respectively represented by the amino acids 517-575, 605-663, and 748-795 of the sequence SEQ ID NO: 3) and fragments corresponding to the fragments 182-206 and 66-147 of the Nef protein of the Bru/LAI HIV-1 isolate (these fragments are respectively represented by the amino acids 577-601 and 665-746 of the sequence SEQ ID NO: 3).

The object of the present invention is also a recombinant vector containing a polynucleotide according to the invention.

Preferably, a recombinant vector according to the invention is an expression vector; advantageously this is a vaccinal vector.

Very many vaccinal vectors, notably usable within the scope of anti-HIV vaccination, are known per se. As examples, mention will be made of vectors with naked DNA, as well as recombinant viral vectors. Among the latter, will notably be mentioned: vectors derived from poxvirus, such as for example vaccinia virus, such as NYVAC (New-York vaccinia), and MVA (modified virus Ankara), or aviary poxviruses such as canarypox; vectors derived from adenoviruses, such as the adenovirus of type 5 (Ad5); vectors derived from alphaviruses, myxomaviruses, or from defective herpes viruses.

According to a preferred embodiment of the present invention, said vector is derived from a vaccinia virus, and advantageously from the MVA virus. This virus, which derives from the Ankara strain of the vaccinia virus, was strongly attenuated by 574 passages on chicken embryo fibroblasts, subsequently to which it lost the capacity of efficiently replicating in most mammal cells (an efficient replication is only observed in chicken embryo fibroblasts and BHK-21 cells). This attenuation results from several excisions (excisions I, II, III, IV, and VI) in the viral genome (MEYER et al., J. Gen. Virol., 72 (Part 5), 1031-8, 1991). Exogenous genetic material may be inserted at any of these excisions.

The object of the present invention is also the use of a recombinant vector according to the invention for obtaining an anti-HIV vaccine.

The invention also relates to an immunogenic or vaccinal composition comprising a recombinant vector according to the invention, and a pharmaceutically acceptable carrier. Pharmaceutically acceptable carriers are well-known to one skilled in the art. Reference may notably be made to Remington's text book: The Science and Practice of Pharmacy, 21$^{st}$ edition, Lippincott Williams & Wilkins.

Within this scope, said vector may advantageously be used in association with lipopeptides, for example palmitoyl lipopeptides. Lipopeptides consist of immunogenic fragments of HIV proteins bound in a covalent way to a lipid chain. Lipopeptides usable within the scope of the present invention are for example described in the applications EP0491628, or WO 99/51630. Advantageously, the immunogenic fragments HIV proteins used are fragments homologous to the fragments 17-35 and 253-284 of the Gag protein, to the fragment 325-355 of the Pol protein and to the fragments 66-97 and 116-145 of the Nef protein.

Advantageously, the recombinant vectors according to the invention may be used in association with lipopeptides within the scope of a vaccination of the <<prime-boost>> type, (comprising primo-immunization with a vector according to the invention, followed by a recall with said lipopeptides, or conversely, a primo-immunization with lipopeptides, followed by a recall with a vector according to the invention).

According to another aspect, the invention relates to method for inducing an immune response in a subject requiring it, said method comprising the administration of recombinant vector according to the invention.

The invention also relates to a method for preventing or treating an HIV infection comprising the administration to a subject requiring it of a recombinant vector according to the invention. In particular the infection may be an HIV-1 infection. The recombinant vector is preferentially administered in an immunologically effective amount, i.e. an amount sufficient for inducing a protective or therapeutic immunological response in the subject having received the vector, or the immunogenic or vaccinal composition comprising it.

The present invention is illustrated in a non-limiting way by the figures and examples which follow.

FIG. 1 schematizes the transfer vector pTG16626. BRD3: Right recombination arm (sequence located downstream from the excision III of MVA); BRG3: Left recombination arm (sequence located upstream from the deletion III of MVA); GPT/EGFP: selection marker; BRG3': repetition sequence of BRG3.

Figure 2:
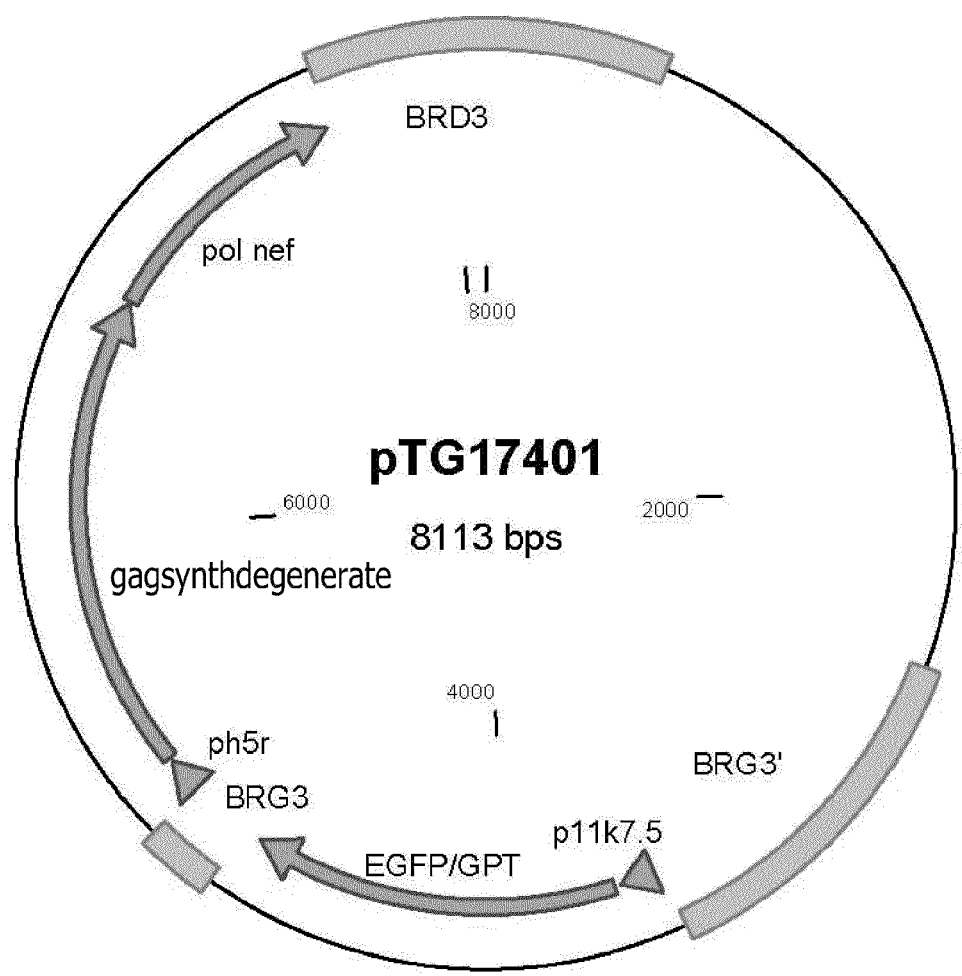

FIG. 2 schematizes the vector pTG17401, resulting from the insertion of the construct gag(degenerate)-pol-nef into pTG16626.

FIG. 3 represents the sequence of the region of the vector pTG17401 comprising the sequence BRG3', the selection cassette containing the fusion gene EGFP/GPT under control of the promoter p11K7.5K, the sequence BRG3, the fusion gene gag(degenerate)-pol-nef under control of the promoter ph5R, and the sequence BRD3.

Figure 4:
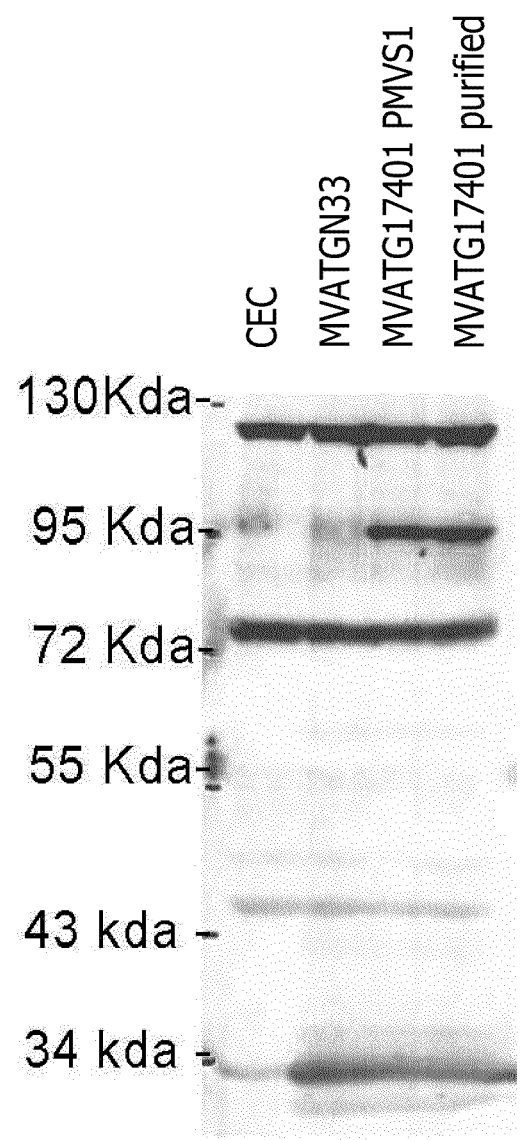

FIG. 4 represents the results of the Western Blot analysis of the expression of gag(degenerate)-pol-nef in chicken embryo cells: CEC: control (non-infected cells); MVATGN33: cells infected with MVATGN33; MVATG17401 PMVS1: cells infected with the primary stock PMVS1 of MVATG17401; purified MVATG17401: cells infected with the purified MVATG17401.

Figure 5:
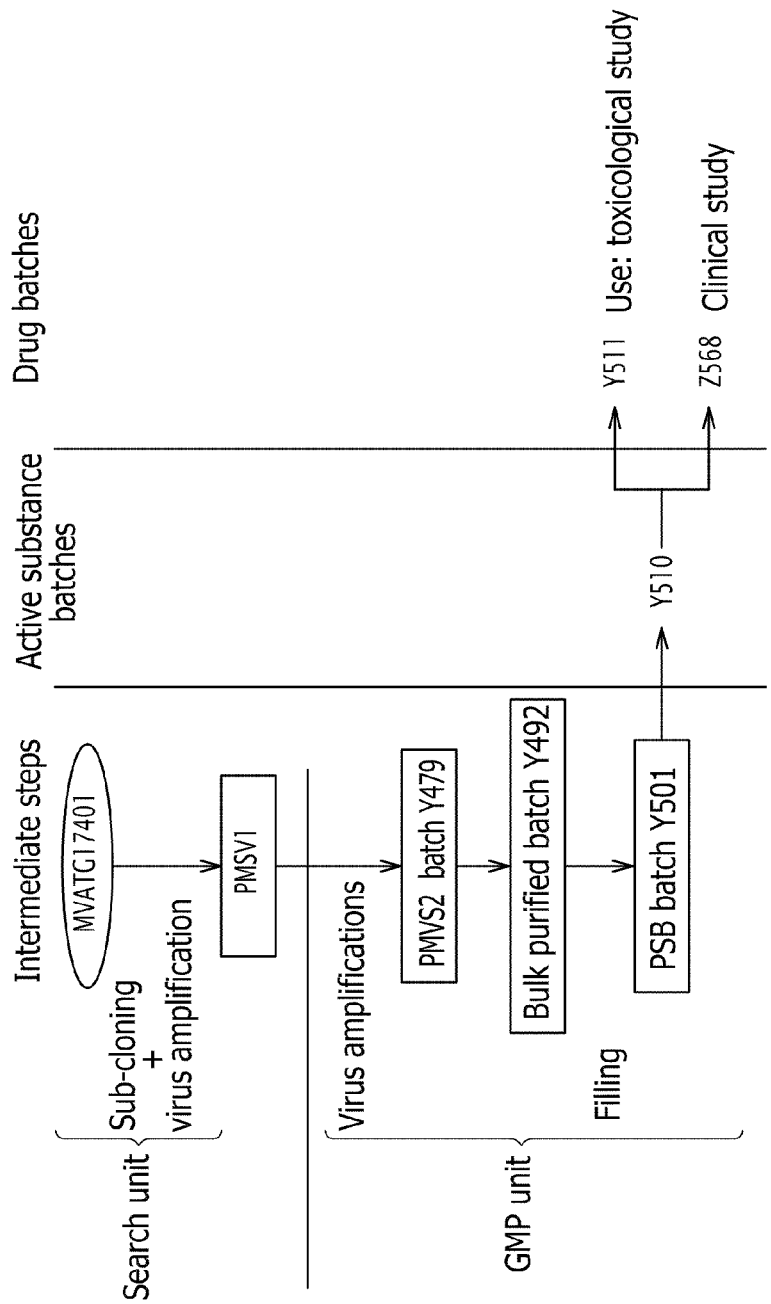

FIG. 5 represents the filiation between the different batches of viruses after subcloning and amplification of the MVATG17401 virus.

EXAMPLE 1

Obtaining a Degenerate Gag Sequence, and a Gag(Degenerate)-Pol-Nef Construct Containing this Sequence The degenerate sequence of gag (SEQ ID NO: 1) was split up into two portions, which were individually assembled by PCR from synthetic oligonucleotides. This assembly generated two fragments, BamHI-EcoRV (fragment 1) and EcoRV-SalI (fragment 2), the EcoRV and SalI sites being an integral part of the modified gag sequence.

Both thereby obtained fragments BamHI-EcoRV and EcoRV-SalI, as well as a fragment SalI-NotI of 851 bp, containing sequences coding for Pol and Nef protein fragments are bound to each other through the ligase T4, and the resulting gag(degenerate)-pol-nef fragment is cloned between the sites BamHI and NotI of the transfer vector pTG16626, described hereafter, and schematized in FIG. 1.

The transfer vector pTG16626 contains an expression cassette formed by a multisite linker allowing insertion of an exogenous sequence under transcriptional control of the promoter ph5R (late/early promoter of the vaccinia virus, SMITH et al., Vaccine.; 11, 43-53, 1993). This cassette is surrounded by the recombination arms BRD3 and BRG3, which correspond to the sequences flanking the excision area III of the MVA virus, and will allow insertion of the cassette into the genome of the MVA at this excision area. This vector further contains a selection cassette based on the expression of the EGFP/GPT (enhanced green fluorescent protein/xanthine-guanine phosphoribosyl transferase of E. Coli) fusion gene placed under the control of the vaccinal promoter p11K75 (synthetic early-late promoter, resulting from the fusion of the late promoter p11K and of the early promoter p7.5K, described for example in the Application EP1146125). The synthesis of xanthine-guanine phosphoribosyl transferase allows the formation of recombinant MVA in a selective medium containing xanthine, mycophenolic acid and hypoxanthine (FALKNER and MOSS, J Virol, 62, 1849-54, 1988) and the synthesis of EGFP allows the viewing of fluorescent plaques. This selection cassette is surrounded by the BRG3 sequence on the one hand, and by a homologous sequence BRG3', on the other hand. Intragenic recombination between these two homologous sequences allows elimination of the selection cassette after several passages of the recombinant MVA in a non-selective medium.

Insertion of the gag(degenerate)-pol-nef fragment into the vector pTG16626 opened by BamHI NoI generates the vector pTG17401, which is schematized in FIG. 2.

The sequence of the region of the vector pTG17401, comprising the sequence BRG3', the selection cassette containing the fusion gene EGFP/GPT under control of the promoter p11K7.5K, the sequence BRG3, the fusion gene gag(degenerate)-pol-nef under control of the promoter ph5R, and the sequence BRD3, is illustrated in FIG. 3 (SEQ ID NO: 4).

EXAMPLE 2

Generation of a Recombinant Vaccinia Virus Expressing the Fusion Gene Gag(Degenerated)-Pol-Nef Generation of the recombinant vaccinia virus is accomplished by homologous recombination between the transfer plasmid pTG17401 and an MVA virus (MVATGN33). The recombinant viruses are selected for their capability of forming lysis plaques in the presence of mycophenolic acid.

The chicken embryo cells used for generating the recombinants were obtained by treating chicken embryos for 2 hrs at 37° C. with TrypLE™ Select (Gibco) solution in an amount of 200 mL for 10 embryos. These cells are then grown in an MBE (Eagle Based Medium, Gibco) medium, added with 5% FCS, 40 µg/L gentamycin at 37° C. 5% $CO_2$.

Falcon 3001 dishes were sown with $1.5 \cdot 10^6$ CECs/dish in MBE medium added with 10% FCS. After 48 hrs of incubation at 37° C., 5% $CO_2$, the cells are infected with MVATGN33 in an amount of 0.02 pfu/cellule, diluted in PBS+ cations (magnesium acetate 100 ug/mL, calcium chloride 100 mg/L)+1% FCS. After 30 min, 2 mL of MBE+5% FCS are added to the infected cells. And they are then incubated for 1 hr at 37° C., 5% $CO_2$. The transfer plasmid pTG17401 (2 and 5 μg) is precipitated from a solution of Hepes and $CaCl_2$. The precipitate is deposited on the previously infected cells. After 1 hr at room temperature, they are incubated after adding 2 mL of MBE+5% FCS, at 37° C., 5% $CO_2$ for 2 hrs.

The cells are washed twice with PBS+ cations and then incubated with 2 mL of MBE+5% FCS at 37° C., 5% $CO_2$. After 48 hrs the dishes are frozen.

Isolation of the viral plates is carried out by thawing out the previous dishes. The contents of the dishes are recovered in 6 mL Falcon tubes. After sonication, serial dilutions ($10^{-1}$ to $10^{-3}$ for the 1$^{st}$ selection and $10^{-3}$ to $10^{-6}$ for the following selections) of these crude extracts are used for infecting CECs.

A layer of 5 mL of gelose MBE medium added with 5% FCS, with a mixture of mycophenolic acid (25 μg/mL, Sigma), xanthine (250 μg/mL, Sigma) and hypoxanthine (15 μg/mL) is deposited in each dish for selecting GPT+ recombinant virus. The dishes are incubated at 37° C., 5% $CO_2$ for 72 hrs. A new layer of 5 mL of gelose MBE medium containing 5% FCS and a mixture of mycophenolic acid, xanthine and hypoxanthine and neutral red is deposited on the previous gelose layer. The dishes are then reincubated until viral plaques appear. The isolated fluorescent viral plaques are amplified on CECs and then analyzed by PCR for seeking the presence of the transgene and detecting contamination by the parent virus MVATGN33. The selected clones are amplified on CEC and then sub-cloned on a selected medium as described above, until complete removal of the wild virus MVATGN33.

The selection marker EGFP/GPT is then removed by several passages on a non-selective medium. This removal is obtained by intragenic recombination between the homologous sequences surrounding the selection cassette.

After verifying the presence of the gene gag(degenerate)-pol-nef, of the absence of the EGFP/GPT, and of the absence of contamination by the wild virus MVATGN33, a clone, designated hereafter as MVATG17401 was selected for generating the primary stock of recombinant viruses (designated as PMVS1). This stock is made up as follows: 100 μL of amplification of the selected clone are used for infecting 2 F175 flasks containing CECs (50 mL at $OD_{560nm}$=0.23-0.24/F175) grown for 48 hrs. Each flask contains 25 mL of medium MBE+5% FCS. They are incubated for 72 hrs at 37° C., 5% $CO_2$ and are then frozen. After thawing and sonication, this stock is titered on CEC and used as a seed for producing purified virus.

For the production of the purified recombinant virus, F500 flasks sown with CECs grown in VP-SFM are infected with the primary stock in an amount of 0.02 pfu/cell in MBE medium without any serum for 72 hrs at 37° C., 5% $CO_2$. The infected cells are harvested after centrifugation and then frozen. The centrifugation supernatants are kept at 4° C. The virus is then purified on two consecutive cushions of 36% saccharose followed by a saccharose gradient (30% to 45%). The viral bands are sampled and diluted in 10 mM Tris at pH8 to ⅓. After centrifugation at 4500 rpm for 18 hrs, the viral pellet is taken up in buffer and then tittered on CEC.

EXAMPLE 3

Expression of Gag(Degenerate)-Pol-Nef in Chicken Embryo Fibroblasts

Falcon F3001 Petri dishes are sown at day-1 with 1.5.10$^6$ CECs/dish and then infected in an amount of 0.2 pfu/cell in MBE medium+5% FCS and incubated at 37° C., 5% $CO_2$.

After 24 hrs, the supernatant is removed and the cells are taken up in 300 μL of Tris-Glycine 2× buffer (ref: LC2676; Novex) added with 5% β-mercapto-ethanol. The lysate is transferred into an Eppendorf tube, sonicated and heated for 5 min at 100° C. 10% of the material is subject to electrophoresis on an acrylamide gel (8%) under denaturating and reducing conditions in LaemmLi buffer.

The proteins are then transferred on a PVDF membrane (Macherey Nagel) by electrophoresis at 150 mA for 16 hrs in 25 mM Tris buffer, 192 mM glycine, 20% methanol The membranes are saturated in a saturation buffer PBS 1×, Tween 20 0.5%, FCS 5% for 2 Hrs.

The membranes are then put for 2 hrs in the presence of the primary antibody (polyclonal serum from a pool of immunized patients with a mixture of HIV peptide fragments containing peptides homologous to the fragments 66-97, 117-147 and 182-205 of the Nef protein, to the fragments 183-214 and 253-284 of the Gag protein, and to the fragment 303-335 of the Env protein), diluted to 1/3000 in the saturation buffer. Next, the membranes are washed three times in PBS1× washing buffer for 10 min. The membranes are then put into the presence of the secondary antibody, biotinylated human anti-IgG antibodies (Amersham) diluted to 1/500 in the saturation buffer for 1 hr. They are washed as earlier. The membranes are finally put for 30 min in the presence of a streptavidin-biotinylated peroxidase complex (Amersham) diluted in the saturation buffer to 1/1000. Development is accomplished with the ECL (Enhanced Chemiluminescence, Amersham) kit.

The results are illustrated by FIG. 4.

In spite of the low specificity of the human polyclonal serum used, which recognizes a MVATGN33 protein which quasi migrates at the same level as the fusion protein Gag-Pol-Nef, these results show that the expression cassette of gag(degenerate)-pol-nef contained in the MVATG17401 virus is functional. The fusion protein expressed from this vector is located at about 100 kDa (theoretically 97 kDa) which corresponds to the expected molecular weight for the Gag-Pol-Nef fusion protein.

Sequencing of the insert in the MVATG17401 virus containing the ORF coding for the fusion protein Gag-Pol-Nef has shown that the fusion protein consists of 795 amino acids and is identical with the expected theoretical sequence.

EXAMPLE 4

Genetic Stability of the MVATG17401 Recombinant Vector at Passage Levels Equivalent to the Clinical Batch The genetic stability of the MVATG17401 recombinant vector at a passage level equivalent to the clinical batch was evaluated. For this, a quality batch GMP, directly derived from the primary seed batch (PSB), was analyzed by PCR, Western blot and sequencing. More than 100 individual plates isolated from the same material were analyzed by Western blot in order to check the genetic stability of the MVATG17401 recombinant vector.

Materials and Methods

GMP Material

The expression of the fusion protein was analyzed by Western blot for the PSB (batch Y501), the bulk material of the toxicological batch before filling (X511E03) and of the clinical batch (Z568). The filiation of the batches is shown in FIG. 5. PCR analysis and sequencing were carried on the isolated DNA of the toxicology batch after filling (Y511). Analysis of the expression of the fusion protein by Western blot was also applied on individual isolated clones from the bulk material of the toxicological batch (X511E03).

Characterization of the Genetic Insert by PCR

Two pairs of primers were used for covering the whole of the expression cassette and of the flanking viral sequences. The size of the amplified fragments is 1682 bp (PCR fragment A, sense primer: CATGACGAGCTTCCGAGTTC (SEQ ID NO:5), anti-sense primer: GTTGAAGCACTTCACCATCT-TCCTCTG (SEQ ID NO:6)) and 1833 bp (PCR fragment B, sense primer: CCTGAACAAGATCGTGAGGATG (SEQ ID NO:7), anti-sense primer: GCTCCTTATACCAAGCACTC (SEQ ID NO:8)).

Western Blot

Infected A549 cells were lyzed with LDS buffer in the presence of β-mercaptoethanol. The proteins were separated by electrophoresis on 10% polyacrylamide gel and transferred onto a PVDF membrane. The polyprotein was detected with a murine monoclonal antibody directed against the Gag protein of the HIV-1 (anti-HIV-1-p24). Murine anti-body goat antibodies bound to biotin and a streptavidin-peroxidase complex were used for labelling.

Sub-Cloning and Determination of the Proportion of Clones Expressing the Fusion Protein Plates of the MVATG17401 vector were isolated from layers of BHK cells infected with the bulk material of the toxicological batch (X511E03) and covered with agarose. A total of 113 plates was isolated and amplified in two successive cycles in 96-well plates. A plate suspected of being contaminated was discarded following the analysis. The other plates were used for infecting A549 cells in order to express the fusion protein.

Specificity of the Monoclonal Antibodies Used for Immunodetection

The anti-HIV-1-p24 murine monoclonal antibody (1A) is from Perkin Elmer (ref: NEA-9306). It was produced against a purified lysate of the HTLV-111 B strain of the HIV-1. This antibody is specific to the structural protein of the core p24 coded by gag and to the precursor Gag p55.

RESULTS

Characterization of the genetic insert on the isolated DNA from the toxicological batch (Y511) shows that the size of the fragments A and B amplified by PCR and the sequence of the insert comply with expectations.

The proportion of viruses which express the fusion protein was determined on a sample of the toxicological batch before filling (X511E03) and show that 100% of the clones express the fusion protein.

Further, expression of the fusion protein was evaluated in samples of the primary seed batches (PSB), the toxicological batch (X511E03) and clinical batch (Z568). The fusion protein was detected in all the samples, without any difference having been detected with the positive control sample while the fusion protein was undetectable in negative control samples.

These results show that the vector MVATG17401 is genetically stable at the passage of the clinical batch Z568 which therefore validates the use of the primary seed batch for producing clinical batches at the same passage level as Z568.

The invention claimed is:

1. A polynucleotide encoding the HIV-1 Gag (p55) protein, comprising the sequence SEQ ID NO: 1.

2. A recombinant vector comprising a polynucleotide according to claim 1.

3. The recombinant vector according to claim 2, wherein said vector is an attenuated poxvirus.

4. The recombinant vector according to claim 3, wherein said poxvirus is the modified Ankara virus (MVA).

5. An immunizing composition comprising a recombinant vector according to claim 2.

6. A method for inducing an immune response in a subject comprising the administration to a subject requiring it of a recombinant vector according to claim 2.

7. A recombinant vector according to claim 2, wherein the polynucleotide encodes a fusion protein comprising the HIV-1 Gag (p55) protein fused with at least another HIV polypeptide.

8. A recombinant vector according to claim 7, wherein said HIV polypeptide is selected from the group consisting of the Pol protein, the Nef protein, the Env protein and any fragment of said proteins bearing at least one epitope recognized by anti-HIV antibodies or by anti-HIV cytotoxic T lymphocytes (CTLs).

9. A recombinant vector according to claim 7, wherein said polynucleotide has the sequence SEQ ID NO: 2.

10. An immunizing composition comprising a recombinant vector according to claim 7.

11. A method for inducing an immune response in a subject comprising the administration to a subject requiring it of a recombinant vector according to claim 7.

* * * * *

SEQUENCE LISTING

```
<160> NUMBER OF SEQ ID NOS: 8

<210> SEQ ID NO 1
<211> LENGTH: 1543
<212> TYPE: DNA
<213> ORGANISM: Artificial
<220> FEATURE:
<223> OTHER INFORMATION: synthetic GAG Gene

<400> SEQUENCE: 1
atgggcgcca gggccagcgt gctgagcgga ggcgagctgg acaggtggga gaagatcagg      60
ctgaggcctg gaggcaagaa gaagtataag ctgaagcaca tcgtgtgggc cagcagggag     120
ctggagaggt tcgccgtgaa ccctggcctg ctggagacca gcgagggctg caggcagatc     180
ctgggccagc tgcagcccag cctgcagacc ggcagcgagg agctgaggag cctgtacaac     240
accgtggcca ccctgtactg cgtgcaccag aggatcgaga tcaaggacac caaggaggcc     300
ctggacaaga tcgaggagga gcagaacaag tccaagaaga aggcccagca ggctgctgcc     360
gacaccggcc acagcagcca ggtgagccag aactacccta tcgtgcagaa catccagggc     420
cagatggtgc accaggccat cagccctagg accctgaacg cctgggtgaa ggtggtggag     480
gagaaggcct tcagccctga ggtgatccct atgttcagcg ccctgagcga gggagccaca     540
cctcaggacc tgaacaccat gctgaacacc gtgggaggcc accaggccgc catgcagatg     600
ctgaaggaga ccatcaacga ggaggctgcc gagtgggaca gggtgcaccc tgtgcacgct     660
ggacccatcg ctccaggcca gatgagggag cccagaggca gcgacatcgc cggcaccacc     720
agcacccctg aggagcagat cggctggatg accaacaacc ctcccatccc tgtgggcgaa     780
atctacaaga ggtggatcat cctgggcctg aacaagatcg tgaggatgta cagccctacc     840
```

| | |
|---|---:|
| agcatcctgg atatcaggca gggccctaaa gagcccttca gggactacgt ggacaggttc | 900 |
| tacaagaccc tgagagccga gcaggccagc caggaggtga agaactggat gaccgagacc | 960 |
| ctgctggtgc agaacgccaa ccctgactgc aagaccatcc tgaaggccct gggacctgct | 1020 |
| gccaccctgg aggagatgat gaccgcctgc agggcgtgg gaggcccagg ccacaaggcc | 1080 |
| agggtgctgg ccgaggccat gagccaggtg accaacaccg ccaccatcat gatgcagaga | 1140 |
| ggcaacttca ggaaccagag gaagatggtg aagtgcttca actgcggcaa ggagggccac | 1200 |
| accgccagga actgcagggc tcccaggaag aagggctgct ggaagtgcgg caaggagggc | 1260 |
| caccagatga aggactgcac cgagaggcag gccaacttcc tgggcaagat ctggcccagc | 1320 |
| tacaagggca ggccaggcaa cttcctgcag agcaggcccg agcccaccgc tccacctttc | 1380 |
| ctgcagagca ggcccgagcc caccgctcct cctgaggaga gcttcaggag cggcgtggag | 1440 |
| acaaccaccc ctcctcagaa gcaggagccc atcgacaagg agctgtaccc tctgaccagc | 1500 |
| ctgaggagcc tgttcggcaa cgaccctagc agccaggagt cga | 1543 |

<210> SEQ ID NO 2
<211> LENGTH: 2388
<212> TYPE: DNA
<213> ORGANISM: Artificial
<220> FEATURE:
<223> OTHER INFORMATION: synthetic gag -nef-pol
<220> FEATURE:
<221> NAME/KEY: CDS
<222> LOCATION: (1)..(2388)

<400> SEQUENCE: 2

| | |
|---|---:|
| atg ggc gcc agg gcc agc gtg ctg agc gga ggc gag ctg gac agg tgg<br>Met Gly Ala Arg Ala Ser Val Leu Ser Gly Gly Glu Leu Asp Arg Trp<br>1               5                  10               15 | 48 |
| gag aag atc agg ctg agg cct gga ggc aag aag aag tat aag ctg aag<br>Glu Lys Ile Arg Leu Arg Pro Gly Gly Lys Lys Lys Tyr Lys Leu Lys<br>               20                  25                30 | 96 |
| cac atc gtg tgg gcc agc agg gag ctg gag agg ttc gcc gtg aac cct<br>His Ile Val Trp Ala Ser Arg Glu Leu Glu Arg Phe Ala Val Asn Pro<br>                       35                  40                45 | 144 |
| ggc ctg ctg gag acc agc gag ggc tgc agg cag atc ctg ggc cag ctg<br>Gly Leu Leu Glu Thr Ser Glu Gly Cys Arg Gln Ile Leu Gly Gln Leu<br>50                  55                  60 | 192 |
| cag ccc agc ctg cag acc ggc agc gag gag ctg agg agc ctg tac aac<br>Gln Pro Ser Leu Gln Thr Gly Ser Glu Glu Leu Arg Ser Leu Tyr Asn<br>65                  70                  75               80 | 240 |
| acc gtg gcc acc ctg tac tgc gtg cac cag agg atc gag atc aag gac<br>Thr Val Ala Thr Leu Tyr Cys Val His Gln Arg Ile Glu Ile Lys Asp<br>                           85                  90                95 | 288 |
| acc aag gag gcc ctg gac aag atc gag gag gag cag aac aag tcc aag<br>Thr Lys Glu Ala Leu Asp Lys Ile Glu Glu Glu Gln Asn Lys Ser Lys<br>                  100               105              110 | 336 |
| aag aag gcc cag cag gct gct gcc gac acc ggc cac agc agc cag gtg<br>Lys Lys Ala Gln Gln Ala Ala Ala Asp Thr Gly His Ser Ser Gln Val<br>            115               120              125 | 384 |
| agc cag aac tac cct atc gtg cag aac atc cag ggc cag atg gtg cac<br>Ser Gln Asn Tyr Pro Ile Val Gln Asn Ile Gln Gly Gln Met Val His<br>        130               135              140 | 432 |
| cag gcc atc agc cct agg acc ctg aac gcc tgg gtg aag gtg gtg gag<br>Gln Ala Ile Ser Pro Arg Thr Leu Asn Ala Trp Val Lys Val Val Glu<br>145                150                155              160 | 480 |
| gag aag gcc ttc agc cct gag gtg atc cct atg ttc agc gcc ctg agc<br>Glu Lys Ala Phe Ser Pro Glu Val Ile Pro Met Phe Ser Ala Leu Ser | 528 |

-continued

```
                       165                 170                 175
gag gga gcc aca cct cag gac ctg aac acc atg ctg aac acc gtg gga       576
Glu Gly Ala Thr Pro Gln Asp Leu Asn Thr Met Leu Asn Thr Val Gly
            180                 185                 190 ggc cac cag gcc gcc atg cag atg ctg aag gag acc atc aac gag gag       624
Gly His Gln Ala Ala Met Gln Met Leu Lys Glu Thr Ile Asn Glu Glu
                195                 200                 205 gct gcc gag tgg gac agg gtg cac cct gtg cac gct gga ccc atc gct       672
Ala Ala Glu Trp Asp Arg Val His Pro Val His Ala Gly Pro Ile Ala
    210                 215                 220 cca ggc cag atg agg gag ccc aga ggc agc gac atc gcc ggc acc acc       720
Pro Gly Gln Met Arg Glu Pro Arg Gly Ser Asp Ile Ala Gly Thr Thr
225                 230                 235                 240 agc acc ctg cag gag cag atc ggc tgg atg acc aac aac cct ccc atc       768
Ser Thr Leu Gln Glu Gln Ile Gly Trp Met Thr Asn Asn Pro Pro Ile
                245                 250                 255 cct gtg ggc gaa atc tac aag agg tgg atc atc ctg ggc ctg aac aag       816
Pro Val Gly Glu Ile Tyr Lys Arg Trp Ile Ile Leu Gly Leu Asn Lys
            260                 265                 270 atc gtg agg atg tac agc cct acc agc atc ctg gat atc agg cag ggc       864
Ile Val Arg Met Tyr Ser Pro Thr Ser Ile Leu Asp Ile Arg Gln Gly
                275                 280                 285 cct aaa gag ccc ttc agg gac tac gtg gac agg ttc tac aag acc ctg       912
Pro Lys Glu Pro Phe Arg Asp Tyr Val Asp Arg Phe Tyr Lys Thr Leu
    290                 295                 300 aga gcc gag cag gcc agc cag gag gtg aag aac tgg atg acc gag acc       960
Arg Ala Glu Gln Ala Ser Gln Glu Val Lys Asn Trp Met Thr Glu Thr
305                 310                 315                 320 ctg ctg gtg cag aac gcc aac cct gac tgc aag acc atc ctg aag gcc      1008
Leu Leu Val Gln Asn Ala Asn Pro Asp Cys Lys Thr Ile Leu Lys Ala
                325                 330                 335 ctg gga cct gct gcc acc ctg gag gag atg atg acc gcc tgc cag ggc      1056
Leu Gly Pro Ala Ala Thr Leu Glu Glu Met Met Thr Ala Cys Gln Gly
            340                 345                 350 gtg gga ggc cca ggc cac aag gcc agg gtg ctg gcc gag gcc atg agc      1104
Val Gly Gly Pro Gly His Lys Ala Arg Val Leu Ala Glu Ala Met Ser
                355                 360                 365 cag gtg acc aac acc gcc acc atc atg atg cag aga ggc aac ttc agg      1152
Gln Val Thr Asn Thr Ala Thr Ile Met Met Gln Arg Gly Asn Phe Arg
    370                 375                 380 aac cag agg aag atg gtg aag tgc ttc aac tgc ggc aag gag ggc cac      1200
Asn Gln Arg Lys Met Val Lys Cys Phe Asn Cys Gly Lys Glu Gly His
385                 390                 395                 400 acc gcc agg aac tgc agg gct ccc agg aag aag ggc tgc tgg aag tgc      1248
Thr Ala Arg Asn Cys Arg Ala Pro Arg Lys Lys Gly Cys Trp Lys Cys
                405                 410                 415 ggc aag gag ggc cac cag atg aag gac tgc acc gag agg cag gcc aac      1296
Gly Lys Glu Gly His Gln Met Lys Asp Cys Thr Glu Arg Gln Ala Asn
            420                 425                 430 ttc ctg ggc aag atc tgg ccc agc tac aag ggc agg cca ggc aac ttc      1344
Phe Leu Gly Lys Ile Trp Pro Ser Tyr Lys Gly Arg Pro Gly Asn Phe
                435                 440                 445 ctg cag agc agg ccc gag ccc acc gct cca cct ttc ctg cag agc agg      1392
Leu Gln Ser Arg Pro Glu Pro Thr Ala Pro Pro Phe Leu Gln Ser Arg
    450                 455                 460 ccc gag ccc acc gct cct cct gag gag agc ttc agg agc ggc gtg gag      1440
Pro Glu Pro Thr Ala Pro Pro Glu Glu Ser Phe Arg Ser Gly Val Glu
465                 470                 475                 480 aca acc acc cct cct cag aag cag gag ccc atc gac aag gag ctg tac      1488
```

-continued

| | | | | | | | | | | | | | | |
|---|---|---|---|---|---|---|---|---|---|---|---|---|---|---|
|Thr|Thr|Thr|Pro|Pro|Gln|Lys|Gln|Glu|Pro|Ile|Asp|Lys|Glu|Leu|Tyr|
| | | |485| | | | |490| | | | |495| |

```
cct ctg acc agc ctg agg agc ctg ttc ggc aac gac cct agc agc cag      1536
Pro Leu Thr Ser Leu Arg Ser Leu Phe Gly Asn Asp Pro Ser Ser Gln
        500                 505                 510 gag tcg acc ggg cca cta aca gaa gaa gca gag cta gaa ctg gca gaa      1584
Glu Ser Thr Gly Pro Leu Thr Glu Glu Ala Glu Leu Glu Leu Ala Glu
            515                 520                 525 aac aga gag att cta aaa gaa cca gta cat gga gtg tat tat gac cca      1632
Asn Arg Glu Ile Leu Lys Glu Pro Val His Gly Val Tyr Tyr Asp Pro
530                 535                 540 tca aaa gac tta ata gca gaa ata cag aag cag ggg caa ggc caa tgg      1680
Ser Lys Asp Leu Ile Ala Glu Ile Gln Lys Gln Gly Gln Gly Gln Trp
545                 550                 555                 560 aca tat caa att tat caa gag cca ttt aaa aat ctg aaa aca gga atg      1728
Thr Tyr Gln Ile Tyr Gln Glu Pro Phe Lys Asn Leu Lys Thr Gly Met
                565                 570                 575 gag tgg aga ttt gat tct aga tta gca ttt cat cac gta gct aga gaa      1776
Glu Trp Arg Phe Asp Ser Arg Leu Ala Phe His His Val Ala Arg Glu
            580                 585                 590 tta cat cct gaa tat ttt aaa aat tgt aag ctt atg gca ata ttc caa      1824
Leu His Pro Glu Tyr Phe Lys Asn Cys Lys Leu Met Ala Ile Phe Gln
        595                 600                 605 agt agc atg aca aaa atc tta gag cct ttt aga aaa caa aat cca gac      1872
Ser Ser Met Thr Lys Ile Leu Glu Pro Phe Arg Lys Gln Asn Pro Asp
610                 615                 620 ata gtt atc tat caa tac atg gat gat ttg tat gta gga tct gac tta      1920
Ile Val Ile Tyr Gln Tyr Met Asp Asp Leu Tyr Val Gly Ser Asp Leu
625                 630                 635                 640 gaa ata ggg cag cat aga aca aaa ata gag gag ctg aga caa cat ctg      1968
Glu Ile Gly Gln His Arg Thr Lys Ile Glu Glu Leu Arg Gln His Leu
                645                 650                 655 ttg agg tgg gga ctt aca acc atg gta ggt ttt cca gta aca cct caa      2016
Leu Arg Trp Gly Leu Thr Thr Met Val Gly Phe Pro Val Thr Pro Gln
            660                 665                 670 gta cct tta aga cca atg act tac aaa gca gct gta gat ctt tct cac      2064
Val Pro Leu Arg Pro Met Thr Tyr Lys Ala Ala Val Asp Leu Ser His
        675                 680                 685 ttt tta aaa gaa aaa gga ggt tta gaa ggg cta att cat tct caa cga      2112
Phe Leu Lys Glu Lys Gly Gly Leu Glu Gly Leu Ile His Ser Gln Arg
690                 695                 700 aga caa gat att ctt gat ttg tgg att tat cat aca caa gga tat ttt      2160
Arg Gln Asp Ile Leu Asp Leu Trp Ile Tyr His Thr Gln Gly Tyr Phe
705                 710                 715                 720 cct gat tgg cag aat tac aca cca gga cca gga gtc aga tac cca tta      2208
Pro Asp Trp Gln Asn Tyr Thr Pro Gly Pro Gly Val Arg Tyr Pro Leu
                725                 730                 735 acc ttt ggt tgg tgc tac aag cta gta cca atg att gag act gta cca      2256
Thr Phe Gly Trp Cys Tyr Lys Leu Val Pro Met Ile Glu Thr Val Pro
            740                 745                 750 gta aaa tta aag cca gga atg gat ggc cca aaa gtt aaa caa tgg cca      2304
Val Lys Leu Lys Pro Gly Met Asp Gly Pro Lys Val Lys Gln Trp Pro
        755                 760                 765 ttg aca gaa gaa aaa ata aaa gca tta gta gaa att tgt aca gag atg      2352
Leu Thr Glu Glu Lys Ile Lys Ala Leu Val Glu Ile Cys Thr Glu Met
770                 775                 780 gaa aag gaa ggg aaa att tca aaa att ggg cct taa                      2388
Glu Lys Glu Gly Lys Ile Ser Lys Ile Gly Pro
785                 790                 795
```

```
<210> SEQ ID NO 3
<211> LENGTH: 795
<212> TYPE: PRT
<213> ORGANISM: Artificial
<220> FEATURE:
<223> OTHER INFORMATION: Synthetic Construct

<400> SEQUENCE: 3
```

| | | | | | | | | | | | | | | |
|---|---|---|---|---|---|---|---|---|---|---|---|---|---|---|
| Met | Gly | Ala | Arg | Ala | Ser | Val | Leu | Ser | Gly | Gly | Glu | Leu | Asp | Arg | Trp |
| 1 | | | | 5 | | | | | 10 | | | | | 15 | |
| Glu | Lys | Ile | Arg | Leu | Arg | Pro | Gly | Gly | Lys | Lys | Tyr | Lys | Leu | Lys |
| | | | 20 | | | | | 25 | | | | | 30 | |
| His | Ile | Val | Trp | Ala | Ser | Arg | Glu | Leu | Glu | Arg | Phe | Ala | Val | Asn | Pro |
| | | 35 | | | | | 40 | | | | | 45 | | | |
| Gly | Leu | Leu | Glu | Thr | Ser | Glu | Gly | Cys | Arg | Gln | Ile | Leu | Gly | Gln | Leu |
| 50 | | | | | 55 | | | | | 60 | | | | | |
| Gln | Pro | Ser | Leu | Gln | Thr | Gly | Ser | Glu | Glu | Leu | Arg | Ser | Leu | Tyr | Asn |
| 65 | | | | | 70 | | | | | 75 | | | | | 80 |
| Thr | Val | Ala | Thr | Leu | Tyr | Cys | Val | His | Gln | Arg | Ile | Glu | Ile | Lys | Asp |
| | | | | 85 | | | | | 90 | | | | | 95 | |
| Thr | Lys | Glu | Ala | Leu | Asp | Lys | Ile | Glu | Glu | Gln | Asn | Lys | Ser | Lys |
| | | | 100 | | | | | 105 | | | | | 110 | |
| Lys | Lys | Ala | Gln | Gln | Ala | Ala | Ala | Asp | Thr | Gly | His | Ser | Ser | Gln | Val |
| | | 115 | | | | | 120 | | | | | 125 | | | |
| Ser | Gln | Asn | Tyr | Pro | Ile | Val | Gln | Asn | Ile | Gln | Gly | Gln | Met | Val | His |
| 130 | | | | | 135 | | | | | 140 | | | | | |
| Gln | Ala | Ile | Ser | Pro | Arg | Thr | Leu | Asn | Ala | Trp | Val | Lys | Val | Val | Glu |
| 145 | | | | | 150 | | | | | 155 | | | | | 160 |
| Glu | Lys | Ala | Phe | Ser | Pro | Glu | Val | Ile | Pro | Met | Phe | Ser | Ala | Leu | Ser |
| | | | | 165 | | | | | 170 | | | | | 175 | |
| Glu | Gly | Ala | Thr | Pro | Gln | Asp | Leu | Asn | Thr | Met | Leu | Asn | Thr | Val | Gly |
| | | | 180 | | | | | 185 | | | | | 190 | | |
| Gly | His | Gln | Ala | Ala | Met | Gln | Met | Leu | Lys | Glu | Thr | Ile | Asn | Glu | Glu |
| | | 195 | | | | | 200 | | | | | 205 | | | |
| Ala | Ala | Glu | Trp | Asp | Arg | Val | His | Pro | Val | His | Ala | Gly | Pro | Ile | Ala |
| 210 | | | | | 215 | | | | | 220 | | | | | |
| Pro | Gly | Gln | Met | Arg | Glu | Pro | Arg | Gly | Ser | Asp | Ile | Ala | Gly | Thr | Thr |
| 225 | | | | | 230 | | | | | 235 | | | | | 240 |
| Ser | Thr | Leu | Gln | Glu | Gln | Ile | Gly | Trp | Met | Thr | Asn | Asn | Pro | Pro | Ile |
| | | | | 245 | | | | | 250 | | | | | 255 | |
| Pro | Val | Gly | Glu | Ile | Tyr | Lys | Arg | Trp | Ile | Ile | Leu | Gly | Leu | Asn | Lys |
| | | | 260 | | | | | 265 | | | | | 270 | | |
| Ile | Val | Arg | Met | Tyr | Ser | Pro | Thr | Ser | Ile | Leu | Asp | Ile | Arg | Gln | Gly |
| | | 275 | | | | | 280 | | | | | 285 | | | |
| Pro | Lys | Glu | Pro | Phe | Arg | Asp | Tyr | Val | Asp | Arg | Phe | Tyr | Lys | Thr | Leu |
| 290 | | | | | 295 | | | | | 300 | | | | | |
| Arg | Ala | Glu | Gln | Ala | Ser | Gln | Glu | Val | Lys | Asn | Trp | Met | Thr | Glu | Thr |
| 305 | | | | | 310 | | | | | 315 | | | | | 320 |
| Leu | Leu | Val | Gln | Asn | Ala | Asn | Pro | Asp | Cys | Lys | Thr | Ile | Leu | Lys | Ala |
| | | | | 325 | | | | | 330 | | | | | 335 | |
| Leu | Gly | Pro | Ala | Ala | Thr | Leu | Glu | Glu | Met | Met | Thr | Ala | Cys | Gln | Gly |
| | | | 340 | | | | | 345 | | | | | 350 | | |
| Val | Gly | Gly | Pro | Gly | His | Lys | Ala | Arg | Val | Leu | Ala | Glu | Ala | Met | Ser |
| | | 355 | | | | | 360 | | | | | 365 | | | |

```
Gln Val Thr Asn Thr Ala Thr Ile Met Met Gln Arg Gly Asn Phe Arg
    370                 375                 380

Asn Gln Arg Lys Met Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
                420                 425                 430

Phe Leu Gly Lys Ile Trp Pro Ser Tyr Lys Gly Arg Pro Gly Asn Phe
            435                 440                 445

Leu Gln Ser Arg Pro Glu Pro Thr Ala Pro Pro Phe Leu Gln Ser Arg
450                 455                 460

Pro Glu Pro Thr Ala Pro Pro Glu Glu Ser Phe Arg Ser Gly Val Glu
465                 470                 475                 480

Thr Thr Thr Pro Pro Gln Lys Gln Glu Pro Ile Asp Lys Glu Leu Tyr
                485                 490                 495

Pro Leu Thr Ser Leu Arg Ser Leu Phe Gly Asn Asp Pro Ser Ser Gln
            500                 505                 510

Glu Ser Thr Gly Pro Leu Thr Glu Glu Ala Glu Leu Glu Leu Ala Glu
        515                 520                 525

Asn Arg Glu Ile Leu Lys Glu Pro Val His Gly Val Tyr Tyr Asp Pro
530                 535                 540

Ser Lys Asp Leu Ile Ala Glu Ile Gln Lys Gln Gly Gln Gly Gln Trp
545                 550                 555                 560

Thr Tyr Gln Ile Tyr Gln Glu Pro Phe Lys Asn Leu Lys Thr Gly Met
                565                 570                 575

Glu Trp Arg Phe Asp Ser Arg Leu Ala Phe His His Val Ala Arg Glu
            580                 585                 590

Leu His Pro Glu Tyr Phe Lys Asn Cys Lys Leu Met Ala Ile Phe Gln
        595                 600                 605

Ser Ser Met Thr Lys Ile Leu Glu Pro Phe Arg Lys Gln Asn Pro Asp
    610                 615                 620

Ile Val Ile Tyr Gln Tyr Met Asp Asp Leu Tyr Val Gly Ser Asp Leu
625                 630                 635                 640

Glu Ile Gly Gln His Arg Thr Lys Ile Glu Glu Leu Arg Gln His Leu
                645                 650                 655

Leu Arg Trp Gly Leu Thr Thr Met Val Gly Phe Pro Val Thr Pro Gln
            660                 665                 670

Val Pro Leu Arg Pro Met Thr Tyr Lys Ala Ala Val Asp Leu Ser His
        675                 680                 685

Phe Leu Lys Glu Lys Gly Gly Leu Glu Gly Leu Ile His Ser Gln Arg
    690                 695                 700

Arg Gln Asp Ile Leu Asp Leu Trp Ile Tyr His Thr Gln Gly Tyr Phe
705                 710                 715                 720

Pro Asp Trp Gln Asn Tyr Thr Pro Gly Pro Gly Val Arg Tyr Pro Leu
                725                 730                 735

Thr Phe Gly Trp Cys Tyr Lys Leu Val Pro Met Ile Glu Thr Val Pro
            740                 745                 750

Val Lys Leu Lys Pro Gly Met Asp Gly Pro Lys Val Lys Gln Trp Pro
        755                 760                 765

Leu Thr Glu Glu Lys Ile Lys Ala Leu Val Glu Ile Cys Thr Glu Met
    770                 775                 780

Glu Lys Glu Gly Lys Ile Ser Lys Ile Gly Pro
```

<210> SEQ ID NO 4
<211> LENGTH: 6000
<212> TYPE: DNA
<213> ORGANISM: artificial
<220> FEATURE:
<223> OTHER INFORMATION: Fragment of vector pTG17401

<400> SEQUENCE: 4

```
aaataaatca tataaaaaat gatttcatga ttaaaccatg ttgtgaaaaa gtcaagaacg      60
ttcacattgg cggacaatct aaaaacaata cagtgattgc agatttgcca tatatggata     120
atgcggtatc cgatgtatgc aattcactgt ataaaaagaa tgtatcaaga atatccagat     180
ttgctaattt gataaagata gatgacgatg acaagactcc tactggtgta tataattatt     240
ttaaacctaa agatgccatt cctgttatta tatccatagg aaaggataga gatgtttgtg     300
aactattaat ctcatctgat aaagcgtgtg cgtgtataga gttaaattca tataaagtag     360
ccattcttcc catggatgtt tccttttta ccaaaggaaa tgcatcattg attattctcc      420
tgtttgattt ctctatcgat gcggcacctc tcttaagaag tgtaaccgat aataatgtta     480
ttatatctag acaccagcgt ctacatgacg agcttccgag ttccaattgg ttcaagtttt     540
acataagtat aaagtccgac tattgttcta tattatatat ggttgttgat ggatctgtga     600
tgcatgcaat agctgataat agaacttacg caaatattag caaaaatata ttagacaata     660
ctacaattaa cgatgagtgt agatgctgtt attttgaacc acagattagg attcttgata     720
gagatgagat gctcaatgga tcatcgtgtg atatgaacag acattgtatt atgatgaatt     780
tacctgatgt aggcgaattt ggatctagta tgttggggaa atatgaacct gacatgatta     840
agattgctct ttcggtggct ggtgagctcg gatctaagct tgtcgacata aaatatagt      900
agaatttcat ttgtttttt ctatgctata ataggatcg atccgataaa gtgaaaaata      960
attctaattt attgcacggt aaggaagtag aatcataaag aaaagcttct gcaggtcgac    1020
atggtgagca agggcgagga gctgttcacc ggggtggtgc ccatcctggt cgagctggac    1080
ggcgacgtaa acggccacaa gttcagcgtg tccggcgagg gcgagggcga tgccacctac    1140
ggcaagctga ccctgaagtt catctgcacc accggcaagc tgcccgtgcc ctggcccacc    1200
ctcgtgacca ccctgaccta cggcgtgcag tgcttcagcc gctaccccga ccacatgaag    1260
cagcacgact tcttcaagtc cgccatgccc gaaggctacg tccaggagcg caccatcttc    1320
ttcaaggacg acggcaacta caagacccgc gccgaggtga agttcgaggg cgacaccctg    1380
gtgaaccgca tcgagctgaa gggcatcgac ttcaaggagg acggcaacat cctggggcac    1440
aagctggagt acaactacaa cagccacaac gtctatatca tggccgacaa gcagaagaac    1500
ggcatcaagg tgaacttcaa gatccgccac aacatcgagg acggcagcgt gcagctcgcc    1560
gaccactacc agcagaacac ccccatcggc gacggccccg tgctgctgcc cgacaaccac    1620
tacctgagca cccagtccgc cctgagcaaa gaccccaacg agaagcgcga tcacatggtc    1680
ctgctggagt tcgtgaccgc cgccgggatc actctcggca tggacgagct gtacaagagc    1740
gaaaaataca tcgtcacctg gacatgttg cagatccatg cacgtaaact cgcaagccga     1800
ctgatgcctt ctgaacaatg gaaaggcatt attgccgtaa gccgtggcgg tctggtaccg    1860
ggtgcgttac tggcgcgtga actgggtatt cgtcatgtcg ataccgtttg tatttccagc    1920
tacgatcaca caaccagcg cgagcttaaa gtgctgaaac gcgcagaagg cgatggcgaa    1980
ggcttcatcg ttattgatga cctggtggat accggtggta ctgcggttgc gattcgtgaa    2040
```

```
atgtatccaa aagcgcactt tgtcaccatc ttcgcaaaac cggctggtcg tccgctggtt    2100
gatgactatg ttgttgatat cccgcaagat acctggattg aacagccgtg ggatatgggc    2160
gtcgtattcg tcccgccaat ctccggtcgc taatctttc aacgcctggc actgccgggc    2220
gttgttcttt ttaacttccc tgcataatta acgatgagtg tagatgctgt tattttgaac    2280
cacagattag gattcttgat agagatgaga tgctcaatgg atcatcgtgt gatatgaaca    2340
gacattgtat tatgatgaat ttacctgatg taggcgaatt tggatctagt atgttgggga    2400
aatatgaacc tgacatgatt aagattgctc tttcggtggc tggtgagctc ggatctttta    2460
ttctatactt aaaaaatgaa aataaataca aaggttcttg agggttgtgt taaattgaaa    2520
gcgagaaata atcataaatt atttcattat cgcgatatcc gttaagtttg ctgcagctgg    2580
atccatgggc gccagggcca gcgtgctgag cggaggcgag ctggacaggt gggagaagat    2640
caggctgagg cctggaggca agaagaagta taagctgaag cacatcgtgt gggccagcag    2700
ggagctggag aggttcgccg tgaacccagg cctgctggag accagcgagg ctgcaggca    2760
gatcctgggc cagctgcagc ccagcctgca gaccggcagc gaggagctga ggagcctgta    2820
caacaccgtg gccaccctgt actgcgtgca ccagaggatc gagatcaagg acaccaagga    2880
ggccctggac aagatcgagg aggagcagaa caagtccaag aagaaggccc agcaggctgc    2940
tgccgacacc ggccacagca gccaggtgag ccagaactac cctatcgtgc agaacatcca    3000
gggccagatg gtgcaccagg ccatcagccc taggaccctg aacgcctggg tgaaggtggt    3060
ggaggagaag gccttcagcc ctgaggtgat ccctatgttc agcgccctga gcagggagc    3120
cacacctcag gacctgaaca ccatgctgaa caccgtggga ggccaccagg ccgccatgca    3180
gatgctgaag gagaccatca cgaggaggc tgccgagtgg acagggtgc accctgtgca    3240
cgctggaccc atcgctccag gccagatgag ggagcccaga ggcagcgaca tcgccggcac    3300
caccagcacc ctgcaggagc agatcggctg gatgaccaac aaccctccca tccctgtggg    3360
cgaaatctac aagaggtgga tcatcctggg cctgaacaag atcgtgagga tgtacagccc    3420
taccagcatc ctggatatca ggcagggccc taaagagccc ttcagggact acgtggacag    3480
gttctacaag accctgagag ccgagcaggc cagccaggag gtgaagaact ggatgaccga    3540
gaccctgctg gtgcagaacg ccaaccctga ctgcaagacc atcctgaagg ccctgggacc    3600
tgctgccacc ctggaggaga tgatgaccgc ctgccaggc gtgggaggcc aggccacaa    3660
ggccagggtg ctggccgagg ccatgagcca ggtgaccaac accgccacca tcatgatgca    3720
gagaggcaac ttcaggaacc agaggaagat ggtgaagtgc ttcaactgcg gcaaggaggg    3780
ccacaccgcc aggaactgca gggctcccag gaagaagggc tgctggaagt gcggcaagga    3840
gggccaccag atgaaggact gcaccgagag gcaggccaac ttcctgggca gatctggcc    3900
cagctacaag ggcaggccag gcaacttcct gcagagcagg cccgagccca ccgctccacc    3960
tttcctgcag agcaggcccg agcccaccgc tcctcctgag gagagcttca ggagcggcgt    4020
ggagacaacc acccctcctc agaagcagga gcccatcgac aaggagctgt accctctgac    4080
cagcctgagg agcctgttcg gcaacgaccc tagcagccag gagtcgaccg gccactaac    4140
agaagaagca gagctagaac tggcagaaaa cagagagatt ctaaaagaac cagtacatgg    4200
agtgtattat gacccatcaa aagacttaat agcagaaata cagaagcagg gcaaggcca    4260
atggacatat caaatttatc aagagccatt taaaaatctg aaaacaggaa tggagtggag    4320
atttgattct agattagcat ttcatcacgt agctagagaa ttacatcctg aatatttaa    4380
```

-continued

| | |
|---|---|
| aaattgtaag cttatggcaa tattccaaag tagcatgaca aaaatcttag agcctttag | 4440 |
| aaaacaaaat ccagacatag ttatctatca atacatggat gatttgtatg taggatctga | 4500 |
| cttagaaata gggcagcata gaacaaaaat agaggagctg agacaacatc tgttgaggtg | 4560 |
| gggacttaca accatggtag gttttccagt aacacctcaa gtacctttaa gaccaatgac | 4620 |
| ttacaaagca gctgtagatc tttctcactt tttaaaagaa aaaggaggtt tagaagggct | 4680 |
| aattcattct caacgaagac aagatattct tgatttgtgg atttatcata cacaaggata | 4740 |
| ttttcctgat tggcagaatt acacaccagg accaggagtc agatacccat taacctttgg | 4800 |
| ttggtgctac aagctagtac caatgattga gactgtacca gtaaaattaa agccaggaat | 4860 |
| ggatggccca aaagttaaac aatggccatt gacagaagaa aaaataaaag cattagtaga | 4920 |
| aatttgtaca gagatggaaa aggaagggaa aatttcaaaa attgggcctt aagcggccgc | 4980 |
| cccgggagat ctcgatccgg aaagttttat aggtagttga tagaacaaaa tacataattt | 5040 |
| tgtaaaaata aatcactttt tatactaata tgacacgatt accaatactt ttgttactaa | 5100 |
| tatcattagt atacgctaca ccttttcctc agacatctaa aaaaataggt gatgatgcaa | 5160 |
| ctttatcatg taatcgaaat aatacaaatg actacgttgt tatgagtgct tggtataagg | 5220 |
| agcccaattc cattattctt ttagctgcta aaagcgacgt cttgtatttt gataattata | 5280 |
| ccaaggataa aatatcttac gactctccat acgatgatct agttacaact atcacaatta | 5340 |
| aatcattgac tgctagagat gccggtactt atgtatgtgc attctttatg acatcgccta | 5400 |
| caaatgacac tgataaagta gattatgaag aatactccac agagttgatt gtaaatacag | 5460 |
| atagtgaatc gactatagac ataatactat ctggatctac acattcaccg gaaactagtt | 5520 |
| ctgagaaacc tgattatata gataattcta attgctcgtc ggtattcgaa atcgcgactc | 5580 |
| cggaaccaat tactgataat gtagaagatc atacagacac cgtcacatac actagtgata | 5640 |
| gcattaatac agtaagtgca tcatctggag aatccacaac agacgagact ccggaaccaa | 5700 |
| ttactgataa agaagaagat catacagtta cagacactgt ctcatacact acagtaagta | 5760 |
| catcatctgg aattgtcact actaaatcaa ccaccgatga tgcggatctt tatgatacgt | 5820 |
| acaatgataa tgatacagta ccatcaacta ctgtaggcgg tagtacaacc tctattagca | 5880 |
| attataaaac caaggacttt gtagaaatat ttggtattac cgcattaatt atattgtcgg | 5940 |
| ccgtggcaat attctgtatt acatattata tatataataa acgttcacgt aaatacaaag | 6000 |

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
catgacgagc ttccgagttc                                           20

<210> SEQ ID NO 6
<211> LENGTH: 27
<212> TYPE: DNA
<213> ORGANISM: Artificial
<220> FEATURE:
<223> OTHER INFORMATION: primer

<400> SEQUENCE: 6
gttgaagcac ttcaccatct tcctctg                                   27

```
<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
cctgaacaag atcgtgagga tg                                              22

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8 gctcettata ccaagcactc                                                 20
```